(12) United States Patent
Damavarapu et al.

(10) Patent No.: US 7,304,164 B1
(45) Date of Patent: Dec. 4, 2007

(54) MELT-CAST EXPLOSIVE MATERIAL

(75) Inventors: Reddy Damavarapu, Hackettstown, NJ (US); C. Rao Surapaneni, Long Valley, NJ (US); Nathaniel Gelber, Randolph, NJ (US); Raja G. Duddu, Hackettstown, NJ (US); MaoXi Zhang, Flanders, NJ (US); Paritosh R. Dave, Bridgewater, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/549,146

(22) Filed: Oct. 13, 2006

Related U.S. Application Data

(60) Provisional application No. 60/596,697, filed on Oct. 13, 2005.

(51) Int. Cl.
*C07D 233/28* (2006.01)
(52) U.S. Cl. .................................. 548/327.5
(58) Field of Classification Search ............. 548/327.5
See application file for complete search history.

(56) References Cited

OTHER PUBLICATIONS

Cho et al., synthesis and characterization of 1-methyl -2,4,5-trinitroimidazole, (Journal of Heterocyclic chemistry (2002), 39 (1), 141-147.*

Kerusov et al., Heterocyclic nitro compounds using dimethyl sulfate, (Khimiya Geterotsiklicheskikh Sodinenii (1974), (II).*

* cited by examiner

*Primary Examiner*—J. Parsa
(74) *Attorney, Agent, or Firm*—Robert Charles Beam

(57) ABSTRACT

1-Methyl-2,4,5-Trinitroimidazole is synthesized starting from 4-nitroimidazole using stepwise nitration method and further methylation using Dimethylsulphate. It is relatively insensitive to impact and its thermal stability is excellent. The calculated detonation properties indicate that its performance is about 30% better than TATB. It can be prepared easily, with reasonable yield, starting from commercially available Imidazole. Results from impact sensitivity, friction sensitivity, time-to-explosion temperature and vacuum stability tests indicate that it is less sensitive than both RDX and HMX. The good oxygen balance and measured heat of formation data of this material indicate that its propellant performance should be good.

2 Claims, No Drawings

MELT-CAST EXPLOSIVE MATERIAL

CROSS REFERENCE TO RELATED APPLICATIONS

This Application claims priority of U.S. Provisional Application No. 60/596,697, filed Oct. 13, 2005.

STATEMENT REGARDING FEDERALLY SPONSORED RESEARCH OR DEVELOPMENT

The invention described herein may be made, used, or licensed by or for the United States Government for Government purposes without the payment of any royalties thereon or therefore.

BACKGROUND OF THE INVENTION

The present invention relates to a method for the preparation of 1-methyl-2,4,5-trinitroimidazole. In particular, the present invention relates to a method for the preparation of 1-methyl-2,4,5-trinitroimidazole, which method comprises the steps of:

(a) preparing and purifying a quantity of 2,4-dinitroimidazole from commercially available 4-nitroimidazole by conventional methods;

(b) sequentially treating the 2,4-dinitroimidazole of step (a) to prepare 1-methyl-2,4,5-trinitroimidazole by the alternative steps of:

(1) further nitration by combining with concentrated nitric acid and slowly adding sulfuric acid; and (2) methylation by combining and heating with dimethylsulfate;

to obtain 1-methyl-2,4,5-trinitroimidazole.

DESCRIPTION OF RELATED ART

In modern ordnance there is a strong requirement for explosives having good thermal stability, impact insensitivity and explosive performance. However, these requirements are somewhat mutually exclusive. Those explosives having good thermal stability and impact insensitivity exhibit poorer explosive performance and vice versa. The energetic 1-methyl-2,4,5-trinitro Imidazole (MTNI) has both good thermal stability and impact insensitivity as will be described and documented below. TNT has been the mainstay of melt-castable formulations. However, the low density of TNT compared to the main HE fill results in lower performance of the resulting mix. In order to overcome the above-mentioned problems with the existing melt-cast explosive formulations and to meet the U.S. Department of Defense requirements for future high performance munitions systems, it is critical to develop other promising candidates, which possess properties superior to TNT, in an environmentally benign manner. A number of polynitroazoles have been reported in the literature that are thermally stable, have higher densities and, in some cases, outstanding insensitivity characteristics. Use of a higher density polynitroazole as the melt-cast matrix replacement for TNT would not only result in a formulation with higher performance but also, by virtue of its higher power contribution, allow for a lower added energetic solids fill resulting in lower sensitivity to unplanned stimuli.

Although these azole derivatives were studied exclusively for their pharmacological medicinal chemistry, the nitro derivatives of this heterocyclic system were not studied for their use in explosives and propellants applications.

BRIEF SUMMARY OF THE INVENTION

It is an object of the present invention to provide a method for the preparation of 1-methyl-2,4,5-trinitroimidazole, which method comprises the steps of:

(a) preparing and purifying a quantity of 2,4-dinitroimidazole from commercially available 4-nitroimidazole by conventional methods;

(b) sequentially treating the 2,4-dinitroimidazole of step (a) to prepare 1-methyl-2,4,5-trinitroimidazole by the alternative steps of:

(1) further nitration by combining with concentrated nitric acid and slowly adding sulfuric acid; and (2) methylation by combining and heating with dimethylsulfate;

to obtain 1-methyl-2,4,5-trinitroimidazole.

The other objects, features and advantages of the present invention will become more apparent in light of the following detailed description of the preferred embodiment thereof.

SUMMARY OF THE INVENTION

According to the present invention, there is provided a method for the preparation of 1-methyl-2,4,5-trinitroimidazole, which method comprises the steps of:

(a) preparing and purifying a quantity of 2,4-dinitroimidazole from commercially available 4-nitroimidazole by conventional methods;

(b) sequentially treating the 2,4-dinitroimidazole of step (a) to prepare 1-methyl-2,4,5-trinitroimidazole by the alternative steps of:

(1) further nitration by combining with concentrated nitric acid and slowly adding sulfuric acid; and (2) methylation by combining and heating with dimethylsulfate;

to obtain 1-methyl-2,4,5-trinitroimidazole.

DETAILED DESCRIPTION OF THE INVENTION

We have discovered new and practical approach to synthesize Methyl Trinitroimidazole without using diazomethane as methylating agent. We have synthesized MTNI in two different methods. The first approach involves the synthesis of potassium salt of trinitroimidazole and methylating using Dimethylsulphate. Second approach involves the methylation of 2,4-Dinitroimidazole to synthesize MDNI (1-Methyl-2,4-Dinitroimidazole) and further nitration to MTNI (1-Methyl-2,4-5-Trinitroimidazole). MTNI can be used as a melt cast ingredient in explosive and in propellant formulations to give more powerful munitions. Yet this material is highly insensitive to impact and shock, which is an extraordinary discovery.

Benefits and advantages of the subject matter include decreased sensitivity of the material, MTNI, used to initiate detonation by shock and impact when compared to that of RDX and TNT, while providing a high detonation pressure, which is equivalent or superior to the aforesaid materials. MTNI also has superior propellant performance, which is demonstrated by initial experimental results. In theory, the reason for this is believed to be that the compound is perfectly oxygen-balanced toward CO, $H_2O$ and $N_2$ molecules. In propellant applications, low molecular weight gaseous products are desirable. The invention as described here allows the preparation of highly insensitive, thermally stable melt-cast compositions containing MTNI. The impact insensitivity, vacuum stability and explosion temperature data show MTNI to be a highly insensitive energetic material for explosive and propellant applications with excellent thermal stability and explosive performance.

According to the present invention, there is provided a method for the preparation of 1-methyl-2,4,5-trinitroimidazole, which method comprises the steps of:

(a) preparing and purifying a quantity of 2,4-dinitroimidazole from commercially available 4-nitroimidazole by conventional methods;

(b) sequentially treating the 2,4-dinitroimidazole of step (a) to prepare 1-methyl-2,4,5-trinitroimidazole by the alternative steps of:

(1) further nitration by combining with concentrated nitric acid and slowly adding sulfuric acid; and (2) methylation by combining and heating with dimethylsulfate;

to obtain 1-methyl-2,4,5-trinitroimidazole.

MTNI has a melting point of 85° C. and is calculated to have 84% power of HMX. It is thermally stable with a DSC exotherm of 318° C., passes vacuum stability test and is relatively insensitive to impact (50-70 cm; compared to 30-32 for HMX). Results of theoretical performance calculations performed with Cheetah 3 are shown in table 1 below and the detonation pressure and velocities represented graphically in FIGS. 1 and 2.

TABLE 1

| Name | Constituent | Wt. Percent | Det. Press Atm. | Det. Vel m/s |
|---|---|---|---|---|
| MTNI | MTNI | 100 | 288.1 | 7997 |
| DNAN | DNAN | 100 | 166 | 6742 |
| TNT | TNT | 100 | 207.5 | 7236 |
| RDX | RDX | 100 | 342.3 | 9045 |
| COMP-B | RDX | 60 | | |
| | TNT | 40 | 284.3 | 8274 |
| COMP-B/DNP | RDX | 60 | | |
| | DNP | 40 | 321 | 8690 |
| OCTOL | HMX | 70 | | |
| | TNT | 30 | 320.5 | 8677 |
| OCTOL/DNP | HMX | 70 | | |
| | DNP | 30 | 351.1 | 9012 |

Calculations show that substituting DNP for TNT in Comp-B and Octol result in enhanced performance formulations.

1-Methyl-2,4,5-trinitroimidazole is known in the literature; its synthesis, shown in Scheme 1, involves sequential nitration of pyrazole.

Scheme 1

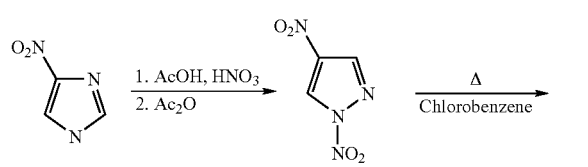

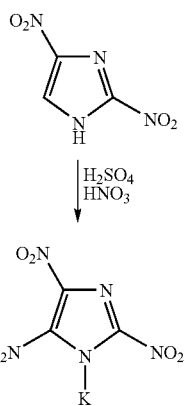

As a part of a program to develop more powerful explosives and propellants, we have discovered a new method for synthesizing MTNI (Scheme 2-3)

Scheme 2

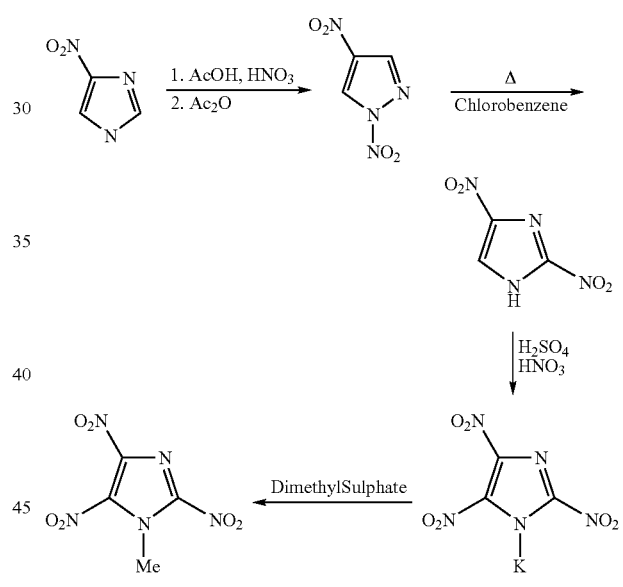

Scheme 3

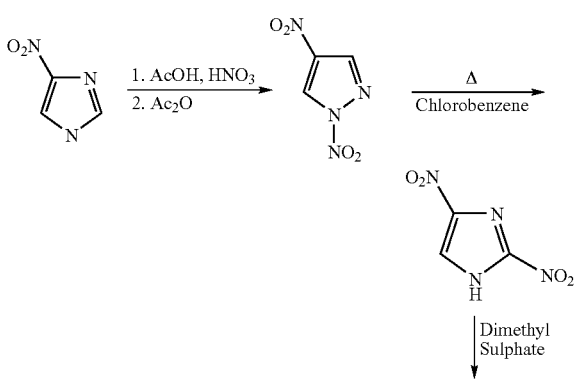

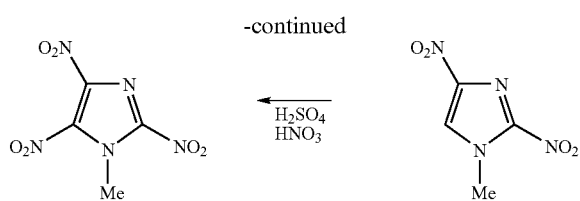

-continued

The starting point for the synthesis of MTNI is 4-nitroimidazole which is commercially available from Aldrich and other chemical suppliers.

The following examples illustrate specific embodiments of the method of carrying out the process and applications as insensitive explosive and propellant. It is to be understood that they are illustrative only and do not in any way limit the invention.

EXAMPLE 1

Purification of 2,4-Dinitroimidazole

Purification of 2,4-Dinitroimidazole (2,4-DNI) containing 4-Nitroimidazole (4-NI) as an impurity. The percent impurity is determined by Proton NMR in DMSO-d6. A weight of impure sample is taken up in a volume of acetone equivalent to 17 mL per gram of 2,4-DNI and stirred until as much has dissolved as appears possible. the mixture is gravity filtered through #41 Whatman filter paper and reduced in volume on a hot plate to approximately 0.45 (hot volume) of the original volume. The solution is covered with Aluminum foil and allowed to come to room temp. The bed of crystals is crushed with a flat-ended glass rod and filtered through #40 Whatman filter paper on a Buchner funnel The filter bed is transferred to a tared weighing paper and air-dried. 2,4-DNI has been obtained with 4-NI contents of approx. 0.5-1.0 wt. % starting with 2,4-DNI containing approx 4-6 wt. % 4-NI

EXAMPLE 2

Preparation of Potassium Salt of 2,4-5-Trinitroimidazole 7.34 g of 99.5% 2,4-Dinitroimidazole (2,4-DNI) [46.2 mmol] was added, in portions, to 24 mL of somewhat cooled, stirring 100% nitric acid in a 100 mL round-bottom flask. A condenser was affixed and the solution was refluxed for 5 minutes in a preheated 100 deg. oil bath. The solution was cooled in an ice-bath and, with stirring, 33 mL of conc. sulfuric acid was slowly added. This was refluxed for 15 minutes The clear, cooled solution was poured over approx. 200 mL of chopped ice. The stirred mixture was brought to pH 0.5-1.0 (pH meter) by portion-wise addition of a well-stirred suspension of aqueous sodium bicarbonate. (83 g sodium bicarbonate plus 600 ml water.) Approx. 90% of the suspension was used. The acid solution was extracted with 7×75 mL ether. The combined extracts were dried over sodium sulfate. The combined 525 mL extract was vacuum-concentrated to approx. 175 mL and, with stirring, a saturated aqueous solution of 1:1 potassium chloride/potassium carbonate was added until the ether phase was approximately pH 6 (pH paper) and the aqueous phase was approximately pH 8-9 and the bubbling had stopped. This was filtered through fast filter paper on a Buchner funnel, washed with a minimum of ice-cold acetone and air-dried. A second crop was obtained by treating the combined 250 mL extract as for Crop 1 except that the volume was first reduced to approx. 75 mL. This yielded 4.60 grams Proton NMR (DMSO-d6); No peaks Carbon 13 NMR(DMSO-d6); 137.823, 146.292 DMSO-d6) 39.414(7)

EXAMPLE 3

Methylation of Potassium Salt of 2,4-5 trinitroimidazole

Preparation of 1-methyl 2,4,5-trinitroimidazole: A mixture of potassium salt of trinitroimidazole (100 mg, 0.41 mmol) and dimethylsulfate (1.0 g, excess) was heated in a preheated oil bath at 80° C. for about 2 h. The reaction mixture was diluted with water (50 mL) and extracted with ether (3×25 mL). The combined organic layer was washed with water (3×25 mL), brine (1×25 mL) and dried ($Na_2SO_4$). The solvent was evaporated under reduced pressure and the pale yellow syrupy residue thus obtained was purified via Si-gel column chromatography (eluent: 10% ethyl acetate-hexane). The pure product (64 mg, 71%) was obtained as a pale yellow solid. m.p: 84-85° C.; DSC: 84.81° C. (5° C./min); $^1H$ NMR (Acetone-$d_6$): 4.37 ppm; $^{13}C$ NMR (Acetone-$d_6$): 37.64, 133.46 (t), 136.05 (br) and 139.97 (t).

EXAMPLE 4

Preparation of 1-Methyl 2,4-5 Trinitroimidazole

Nitration of 1-methyl-2,4-dinitroimidazole with nitric acid and sulfuric acid Fuming nitric acid (4.0 ml, excess, d. 1.544 g/ml) was added to 1-methyl-2,4-dinitroimidazole (0.40 g, 2.33 mmol) at room temperature, following by sulfuric acid (2.0 ml, fuming 30% $SO_3$) with stirring. The reaction temperature was then brought to 105° C. within 25 minutes and kept the temperature for further 2.0 hours. The reaction mixture was poured onto ice and the product was extracted with methylene chloride (3×20 ml). The combined organic phase was washed with water (15 ml), 10% aq. $NaHCO_3$ (15 ml), and water (15 ml) and dried over $Na_2SO_4$. Evaporation of the solvent gave 1-methyl-2,4,5-trinitroimidazole as white solid, 110 mg (21%). $^1H$ NMR (400 MHz, acetone-$d_6$) δ 4.37. $^{13}C$ NMR (100 MHz, acetone-$d_6$) δ 139.9, 136.1, 133.4, 37.7.

EXAMPLE 5

Preparation of 1-Methyl 2,4-5 Trinitroimidazole

Nitration of 1-methyl-2,4-dinitroimidazole with $NO_2BF_4$

Nitronium tetrafluoroborate ($NO_2BF_4$, 5.0 g, 37.6 mmol) was added to the solid of 1-methyl-2,4-dinitroimidazole (4.0 g, 23.3 mmol) at room temperature. Then the reaction temperature was brought to 105° C. within 15 minutes. At that temperature, all solids melted. The reaction mixture was then stirred at that temperature for 1.5 hrs, then cooled to room temperature and diluted with methylene chloride before being poured onto ice/water. The product was extracted with methylene chloride (3×60 ml). The combined organic phase was washed successively with water (50 ml), 10% aq. $NaHCO_3$ (30 ml), and water (50 ml) and dried over $Na_2SO_4$. The solvent was removed in vacuo and the residue was recrystallized with ethanol to give 3.72 g (74%) of 1-methyl-2,4,5-trinitroimidazole as pale yellow crystals, mp=84.0-85.0° C. (literature, mp=82° C.). The structure of the compound was confirmed by NMR spectroscopy.

EXAMPLE 6

Preparation of 1-Methyl 2,4-Dinitroimidazole

Nitration of 1-methylimidazole with Nitric Acid and Sulfuric Acid

Fuming nitric acid (1.5 ml, excess, d.1.544 g/ml) was added to 1-methylimidazole (100 mg, 1.22 mmol) at room temperature with stirring. Then sulfuric acid (1.5 ml, excess, fuming 30% $SO_3$) was added slowly from the top of condenser. After addition, the reaction mixture was heated to 110° C. and then the reaction temperature was maintained between 110-120° C. for 2.0 hrs. The reaction mixture was cooled to room temperature and the resulting mixture of products was extracted with methylene chloride and the organic phase was dried with $Na_2SO_4/NaHCO_3$. Evaporation of the solvent gave 61 mg of oil. Proton NMR showed that the ratio of the products was 7:25:45:2:1 (corresponding to 1-methyl-4-nitroimidazole, 1-methyl-2-nitroimidazole, 1-methyl-4,5-dinitroimidazole, 1-methyl-2,4-dinitroimidazole, and 1-methyl-2,4,5-trinitroimidazole). The yield of 1-methyl-2,4,5-trinitroimidazole is less then 1% based on the integration of the NMR.

EXAMPLE 7

Preparation of 1-Methyl 2,4-5 Trinitroimidazole

Nitration of 1-methylimidazole with Nitronium Tetrafluoroborate

1-Methylimidazole (0.77 g, 9.36 mmol) was dissolved in 10 ml of nitromethane. The solution was then cooled down to −20° C. $NO_2BF_4$ (3.0 g) was added with vigorous stirring. After 10 minutes, the cooling bath was replaced with oil bath (22° C.) and another portion of nitronium tetrafluoroborate (5.0 g, total 8.0 g, 60.0 mmol) was added with stirring. After being stirred at the temperature for 1.0 hour, the reaction mixture was heated to 125° C. within 1.0 hour while nitromethane was collected by distillation under atmosphere pressure. Then the reaction mixture was kept at that temperature for a further 1.0 hour and then poured onto ice. The resulting product mixture was extracted with methylene chloride (4×20 ml). The combined organic phase was washed successively with water (20 ml), 10% aq. $NaHCO_3$ (20 ml), and water (20 ml) and dried over $Na_2SO_4$. Evaporation of the solvent gave 0.945 g of oil. Proton NMR showed that it only contained three products with ratio of 2.8:1.0:0.18 (corresponding tol-methyl-4,5-dinitroimidazoel, 1-methyl-2,4,5-trinitroimidazole and 1-methyl-2-nitroimidazole). Thus the yield of 1-methyl-4,5-dinitroimidazole was about 37%, 1-methyl-2,4,5-trinitroimidazole, 13% and 1-methyl-2-nitroimidazole, 6% based on the integration of the NMR spectrum.

Sensitivity Results
Demonstration of Energetic Character

A sample of MTNI was tested for its energetic character by dropping a 2.5 kg weight at various heights. At heights above 70 cm a powerful detonation was observed. This demonstrates that MTNI is an energetic material which can be used as explosive or propellant.

The following evidence will show that the Impact sensitivity of MTNI is less than that of HMX.

| Compound | Impact Sensitivity (cm) |
|---|---|
| HMX | 25 |
| RDX | 30 |
| TNT | 65 |
| MTNI | 70 |

As shown below, the Energy Performance of 3,4-DNP is greater than that of TATB and TNT and somewhat less than that of HMX and RDX.

| Compound | Energy Performance with respect to HMX (calculated) |
|---|---|
| HMX | 1.0 |
| RDX | 0.9 |
| MTNI | 0.8 |
| TATB | 0.6 |
| TNT | 0.5 |

Other features, advantages, and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. A method for the preparation of 1-methyl-2,4,5-trinitroimidazole, which method comprises the steps of:
    (a) preparing and purifying a quantity of 2,4-dinitroimidazole from commercially available 4-nitroimidazole by conventional methods;
    (b) methylating the 2,4-dinitroimidazole of step (a) by combining and heating with dimethylsulfate to obtain 1-methyl-2,4-dinitroimidazole;
    (c) further nitration of said 1-methyl-2,4-dinitroimidazole by combining said 1-methyl-2,4-dinitroimidazole with concentrated nitric acid and slowly adding sulfuric acid to obtain 1-methyl-2,4,5-trinitroimidazole; and,
    (d) recovering said 1-methyl-2,4,5-trinitroimidazole.

2. A method for the preparation of 1-methyl-2,4,5-trinitroimidazole, which method comprises the steps of:
    (a) preparing and purifying a quantity of 2,4-dinitroimidazole from commercially available 4-nitroimidazole by conventional methods;
    (b) further nitration of said 2,4-dinitroimidazole of step (a) by combining said 2,4-dinitroimidazole with concentrated nitric acid and slowly adding sulfuric acid to obtain 2,4,5-trinitroimidazole; and,
    (c) methylating the 2,4,5-trinitroimidazole of step (b) by combining and heating with dimethylsulfate to obtain 1-methyl-2,4,5-trinitroimidazole;
    (d) recovering said 1-methyl-2,4,5-trinitroimidazole.

* * * * *